(12) United States Patent
Esteron

(10) Patent No.: US 10,167,310 B2
(45) Date of Patent: Jan. 1, 2019

(54) SYSTEM AND METHOD FOR PRODUCING INTERLEUKIN RECEPTOR ANTAGONIST (IRA)

(71) Applicant: ESTAR TECHNOLOGIES LTD, Holon (IL)

(72) Inventor: Aaron Esteron, Holon (IL)

(73) Assignee: ESTAR TECHNOLOGIES LTD, Holon (IL)

( * ) Notice: Subject to any disclaimer, the term of this patent is extended or adjusted under 35 U.S.C. 154(b) by 1128 days.

(21) Appl. No.: 14/375,950

(22) PCT Filed: Jan. 29, 2013

(86) PCT No.: PCT/IL2013/050076
§ 371 (c)(1),
(2) Date: Jul. 31, 2014

(87) PCT Pub. No.: WO2013/114359
PCT Pub. Date: Aug. 8, 2013

(65) Prior Publication Data
US 2015/0025223 A1    Jan. 22, 2015

Related U.S. Application Data

(60) Provisional application No. 61/592,622, filed on Jan. 31, 2012.

(51) Int. Cl.
*C07K 1/36* (2006.01)
*C07K 14/545* (2006.01)
(Continued)

(52) U.S. Cl.
CPC .............. *C07K 1/36* (2013.01); *B01D 21/262* (2013.01); *B01D 21/307* (2013.01);
(Continued)

(58) Field of Classification Search
CPC combination set(s) only.
See application file for complete search history.

(56) References Cited

U.S. PATENT DOCUMENTS 6,623,472 B1    9/2003  Reinecke et al.
6,713,246 B1 *  3/2004  Reinecke ............... A61B 5/415
                                                          435/2
(Continued)

FOREIGN PATENT DOCUMENTS

| EP | 1374927 A1 | 1/2004 |
|---|---|---|
| WO | 2010122548 A2 | 10/2010 |
| WO | 2011136606 A2 | 11/2011 |

OTHER PUBLICATIONS

International Search Report and Written Opinion dated Jun. 6, 2013 in corresponding International Application No. PCT/IL2013/050076.

*Primary Examiner* — Philip R Wiest
*Assistant Examiner* — Guy K Townsend
(74) *Attorney, Agent, or Firm* — Pearl Cohen Zedek Latzer Baratz LLP

(57) ABSTRACT

The present invention relates to a system and method for producing high levels of autologous IL-1RA cytokine, comprising: a blood collection vessel (1), a cover (4), a portion of separation gel (2), an anticoagulant portion (3), a plasma collection syringe comprising a sharp needle (9), a buffy coat collection syringe (11) and an incubation tube with cover (15). The blood collection vessel is adapted such that, when containing the whole blood (5), and centrifuged after treatment, yields separation fractions comprising, a first fraction of RBCs sediment (6), a second fraction of said gel (2), a third fraction comprising WBCs, platelets and a fourth fraction of plasma solution (8).

8 Claims, 10 Drawing Sheets

(51) Int. Cl.
  *B01D 21/26* (2006.01)
  *B01D 21/30* (2006.01)
  *A61K 38/20* (2006.01)
  *A61K 35/16* (2015.01)

(52) U.S. Cl.
  CPC ............ *C07K 14/545* (2013.01); *A61K 35/16* (2013.01); *A61K 38/20* (2013.01)

(56) References Cited

U.S. PATENT DOCUMENTS

| | | | |
|---|---|---|---|
| 6,759,188 B2* | 7/2004 | Reinecke | A61B 5/415 424/184.1 |
| 8,753,690 B2* | 6/2014 | Higgins | A61K 9/0019 424/574 |
| 9,119,829 B2* | 9/2015 | Higgins | A61K 35/15 |
| 9,308,224 B2* | 4/2016 | Higgins | A61K 9/0019 |
| 9,701,728 B2* | 7/2017 | Higgins | A61K 9/0019 |
| 2002/0077276 A1* | 6/2002 | Fredeking | A61K 35/14 435/5 |
| 2003/0138910 A1 | 7/2003 | Reinecke et al. | |
| 2004/0156823 A1 | 8/2004 | Reinecke et al. | |
| 2008/0193424 A1* | 8/2008 | McKale | A61K 35/16 424/93.7 |
| 2009/0220482 A1 | 9/2009 | Higgins et al. | |
| 2010/0008992 A1* | 1/2010 | Ichim | A61K 38/18 424/488 |
| 2010/0055087 A1* | 3/2010 | Higgins | A61K 9/0019 424/94.64 |
| 2010/0125236 A1 | 5/2010 | Bare et al. | |
| 2013/0178425 A1* | 7/2013 | Higgins | A61K 35/15 514/16.8 |
| 2014/0271587 A1* | 9/2014 | Landrigan | A61K 38/19 424/93.71 |
| 2014/0271588 A1* | 9/2014 | Landrigan | A61K 38/19 424/93.71 |
| 2014/0271589 A1* | 9/2014 | Matuska | A61K 38/2006 424/93.72 |
| 2014/0271870 A1* | 9/2014 | O'Shaughnessey | A61K 38/1703 424/489 |
| 2014/0274895 A1* | 9/2014 | Binder | A61K 38/19 514/7.6 |
| 2015/0025223 A1* | 1/2015 | Esteron | B01D 21/262 530/351 |
| 2015/0147300 A1* | 5/2015 | Woodell-May | C12N 5/0645 424/93.7 |
| 2016/0000870 A1* | 1/2016 | Higgins | A61K 35/15 424/93.71 |
| 2016/0074479 A1* | 3/2016 | Serbousek | A61K 38/2006 424/85.2 |
| 2016/0136245 A1* | 5/2016 | Toler | A61K 38/1793 424/85.2 |

\* cited by examiner

US 10,167,310 B2

SYSTEM AND METHOD FOR PRODUCING INTERLEUKIN RECEPTOR ANTAGONIST (IRA)

CROSS REFERENCE TO RELATED APPLICATIONS

This application is a national phase of PCT Application Number PCT/IL2013/050076, filed Jan. 29, 2013, which claims priority from U.S. Provisional Application No. 61/592,622, filed Jan. 31, 2012, which are both incorporated by reference in their entirety.

FIELD OF THE INVENTION

This invention relates to systems and methods for producing high levels of autologous interleukin-1 receptor antagonist ("IL-1RA") cytokine as well as the means used therein, in particular in closed systems.

BACKGROUND

Therapeutically-effective proteins, such as autologous IL-1RA cytokine have been known for a long time. Cytokines such as interleukin play an important role in degenerative musculo-skeletal diseases, including osteoarthritis (OA), and a multitude of inflammatory disorders. Agents that inhibit the action of such cytokines have a high therapeutic potential in such diseases. There is a need for simple and rapid means and methods for the preparation of therapeutically active proteins such as the interleukin receptor antagonist (IRA).

US 2004/156823 describes a method for inducing therapeutically-effective protein or protein mixture (such as interleukin 1 receptor antagonist (IL-1RA)) from body fluid in a syringe in which the inner structures of the syringe are coated with inductors such as immunoglobulin, the syringe is incubated, and the therapeutically-effective protein is formed in the body fluid.

In this method, the body fluid is taken with a syringe directly from the subject.

The document presents four examples for inducing IL-1RA.

US 2003/138910 provides methods and means for producing IL-1RA which serve as safe, cost-effective alternatives which can be carried out quickly for the use and for the production of conventional pharmaceutical products.

U.S. Pat. No. 6,623,472 presents a method for inducing therapeutically-effective protein includes a syringe having inner structures coated with an inductor, disposing a therapeutically-effective protein therein with a body fluid and incubating the syringe and its contents.

There is a long unmet need to provide methods and means for producing high levels of interleukin receptor antagonists by a technique that can be carried out quickly for the use and production of pharmaceutical products.

SUMMARY OF INVENTION

There is provided in accordance with a preferred embodiment of the present invention a system for producing autologous IL-1RA cytokine comprising (referring to FIG. 1):
 i. a blood collection tube (1);
 ii. a tube cover (4) for maintaining said tube closed;
 iii. a portion of separation gel (2);
 iv. an anticoagulant portion (3);
 v. a plasma collection syringe comprising a sharp needle (9);
 vi. a buffy coat collection syringe (11); and
 vii. an incubation tube (15) with cover comprising washed and pretreated borosilicate glass beads in a size of about 0.5-5 mm;
wherein said blood collection tube is a vacuum tube; said separation gel and said anticoagulant are in said vacuum tube; said separation gel is adapted as a barrier and as a separating element between separation fractions; further wherein said tube is adapted such that, when containing said whole blood (5), and centrifuged after treatment, yields separation fractions comprising, a first fraction of red blood cells ("RBCs") sediment (6), a second fraction of said gel (2), a third fraction comprising white blood cells ("WBCs") and platelets, and fourth fraction of plasma solution (8), wherein said incubation tube (15) is adapted for incubation for sufficient time and temperature to yield high levels of said autologous IL-1RA cytokine; said incubation tube is selected from the group consisting of: a plastic tube, a glass tube and any combination thereof.

It is another object of the present invention to disclose the system as defined in any of the above, wherein said system further comprises at least one of the following:
 a. a filter unit having pore size of about 0.2-50 μm;
 b. a stopcock adapted as a turning plug which controls the flow of fluid from said plasma collection syringe to said blood collection tube;
 c. a stopcock adapted as a turning plug which controls the flow of fluid from said buffy coat collection syringe to said blood collection tube;
 d. said anticoagulant selected from the group consisting of: a citrate based anticoagulant, EDTA salt, heparin salt based anticoagulant, oxalate based anticoagulant and any combination thereof; and
 e. said separation gel at density of about 1.06-1.09 gr/cm$^3$.

It is another object of the present invention to disclose the system as defined in any of the above, wherein said centrifugation is being performed for about 10 to about 30 minutes.

It is another object of the present invention to disclose the system as defined in any of the above, wherein at least one of the following holds true:
 a. up to 80% of said plasma is discarded from said blood collection tube;
 b. at least 50% of said plasma is discarded from said blood collection tube;
 c. about 80% of said plasma is discarded from said blood collection tube;
 d. a higher potency of said IL-1RA is obtained when plasma portion containing IL-1RI molecules which bind and inhibit IL-1RA, is discarded.

It is another object of the present invention to disclose a syringe system for producing autologous IL-1RA cytokine comprising (referring to FIG. 2):
 a. a blood collection syringe (22);
 b. an anticoagulant portion (20);
 c. a syringe stopper (23);
 d. a sharp syringe needle (21); and
 e. an incubation vessel (30) with cover comprising washed and pretreated borosilicate glass beads in a size of about 0.5-5 mm;
wherein said blood collection syringe (22) includes an anticoagulant portion (21); further wherein said blood collection syringe (22) is adapted such that, when containing said whole blood, and centrifuged after treatment, yields separation fractions comprising, a first fraction of RBCs sediment (25), a second fraction comprising WBCs and platelets (26) and a third fraction of plasma solution (27).

It is another object of the present invention to disclose the system as defined in any of the above, further wherein at least one of the following holds true:
  a. said incubation vessel (30) containing beads, WBCs and a portion of plasma, is incubated for sufficient time and temperature to yield high levels of said autologous IL-1RA cytokine;
  b. said incubation vessel is selected from the group consisting of: plastic tube, glass tube and any combination thereof; and
  c. said incubation vessel comprises washed and pretreated borosilicate glass beads in a size of about 0.5-5 mm.

It is another object of the present invention to disclose the system as defined in any of the above, wherein at least one of the following holds true:
  a. said an anticoagulant is selected from the group consisting of: a citrate based anticoagulant, EDTA salt, heparin salt based anticoagulant, oxalate based anticoagulant and any combination thereof;
  b. said centrifugation is been performed for about 10-30 min.

It is another object of the present invention to disclose the system as defined in any of the above, wherein at least one of the following holds true:
  a. portion of plasma comprising cellular suspension is transferred to said incubation vessel is between about 5% to about 100%;
  b. said portion of plasma comprising cellular suspension transferred to said incubation vessel is up to 5%;
  c. a portion of said RBCs is discarded resulting in a fraction of WBCs as the bottom layer, and a fraction of plasma solution;
  d. a higher potency of said IL-1RA is obtained in said incubation vessel when plasma solution containing IL-1RI molecules, remains in said blood collection syringe.

It is another object of the present invention to disclose a vessel system for producing autologous IL-1RA cytokine comprising (referring to FIG. 4):
  a. a blood collection syringe (55) comprising a sharp needle (55a) and a filter unit (55b);
  b. a filtered blood sample tube (56);
  c. a tube cover (50);
  d. a plasma portion collection syringe with a sharp needle (57); and
  e. an incubation vessel with a cover (58) comprising washed and pretreated borosilicate glass beads in a size of about 0.5-5 mm;
wherein said blood collection syringe (55) comprising a filter (55b) is adapted to be placed in a downward position containing said whole blood, such that said whole blood is passed through said filter (55b), yielding plasma, platelets and RBC mixture (54), said filter adapted to retain a fraction of WBCs on or within said filter (55b); further wherein when said filtered blood sample tube (56) is centrifuged after treatment separation fractions comprising a first fraction of RBCs sediment (41), a second fraction comprising platelets (42) and a third fraction of plasma solution (43) are yielded; further wherein when said filter comprising a fraction of WBCs (55b) is washed with said plasma portion collection syringe (57a) comprising plasma a WBCs fraction (52) is yielded. It is another object of the present invention to disclose the system as defined in any of the above, wherein at least one of the following holds true:

a. said filtered blood sample tube is centrifuged for 10 to about 30 minutes;
  b. said filtered blood sample tube is selected from the group consisting of: a plastic tube, a glass tube, a vacuum tube and any combination thereof; and
  c. said filter unit is selected from the group consisting of: a hydrophobic filter, hydrophilic filter and any combination thereof.

It is another object of the present invention to disclose the system as defined in any of the above, wherein at least one of the following holds true:
  a. said incubation vessel is selected from the group consisting of: a syringe, a plastic tube, a glass tube and any combination thereof;
  b. said incubation is performed at a temperature of 25-37° C. for 6-24 hours; and
  c. said incubation is performed with 5-6% $CO_2$;
  d. said incubation vessel (58) is incubated for sufficient time and temperature to yield high levels of said autologous IL-1RA cytokine;
  e. said incubation vessel is selected from the group consisting of: a syringe, a plastic tube, a glass tube and any combination thereof.

It is another object of the present invention to disclose the system as defined in any of the above, further wherein at least one of the following holds true:
  a. up to 80% of said plasma is discarded from said filtered blood sample tube;
  b. at least 50% of said plasma is discarded from said filtered blood sample tube;
  c. said plasma is discarded about 80% of plasma from said filtered blood sample tube;
  d. a higher potency of said IL-IRA is obtained when plasma portion containing IL-1RI molecules is discarded.

It is another object of the present invention to disclose a vessel system for producing autologous IL-IRA cytokine comprising (referring to FIG. 5):
  a. an incubation vessel (60) comprising washed and pretreated borosilicate glass beads for collection blood sample (60); and
  b. a vessel cover (62);
wherein said vessel additionally comprising anticoagulant with said washed and pretreated borosilicate glass beads in a size of about 0.5-5 mm and whole blood (64) such that when incubated for sufficient time and temperature yield high levels of said autologous IL-IRA cytokine in said solution.

It is another object of the present invention to disclose the system as defined in any of the above, wherein at least one of the following holds true:
  a. said vessel is incubated at a temperature of 25-37° c. for between 6 and 24 hours;
  b. said vessel is incubated with or without 5-6% $CO_2$;
  c. said incubation vessel is selected from the group consisting of: a plastic tube, a glass tube and any combination thereof;
  d. said anticoagulant portion is selected from the group consisting of: a citrate-based anticoagulant, EDTA salt, heparin salt based anticoagulant, oxalate based anticoagulant and any combination thereof.

It is another object of the present invention to disclose a method for producing of autologous IL-IRA cytokine in a closed system, the method comprising steps of:

a. obtaining a vacuum tube system for producing autologous IL-IRA cytokine comprising:
 i. a blood collection vacuum tube;
 ii. a tube cover;
 iii. a portion of separation gel;
 iv. an anticoagulant portion;
 v. a plasma collection syringe comprising a sharp needle;
 vi. a buffy coat collection syringe; and
 vii. an incubation tube with a cover comprising washed and pretreated borosilicate glass beads in a size of about 0.5-5 mm;
b. placing said anticoagulant portion and said portion of separation gel in said vacuum tube; said separation gel is adapted as a barrier and as a separating element between separation fractions
c. filling said blood collection vacuum tube with blood sample;
d. separating by centrifugation there by obtaining separation fractions comprising, a first fraction of RBCs sediment, a second fraction of said gel, a third fraction comprising WBCs, platelets, growth factors and plasma solution fraction;
e. discarding a portion of plasma with said plasma collection syringe comprising a sharp needle;
f. extracting the remaining plasma and WBCs solution with said plasma collection syringe;
g. transferring said solution into said incubation tube; and
h. incubating said incubation tube;
such that a high concentration of said autologous IL-IRA cytokine is obtained.

It is another object of the present invention to disclose the method as defined in any of the above, wherein additionally comprising at least one of the following steps:
 a. providing a filter unit having pores size of about of 0.2-50 μm.
 b. providing said incubation tube selected from the group consisting of: a plastic tube, a glass tube and any combination thereof;
 c. providing said separation gel at density of about 1.06-1.09 gr/cm$^3$; and
 d. said anticoagulant is selected from the group consisting of: a citrate based anticoagulant, EDTA salt, heparin salt based anticoagulant, oxalate based anticoagulant, and any combination thereof.

It is another object of the present invention to disclose the method as defined in any of the above, wherein at least one of the following steps holds true:
 a. discarding up to 80% of plasma from said blood collection vacuum tube;
 b. discarding at least 50% of plasma from said blood collection vacuum tube;
 c. discarding about 80% of plasma from said blood collection vacuum tube;
 d. discarding plasma portion containing IL-1RI molecules thereby, obtaining a higher potency of said IL-1RA.

It is another object of the present invention to disclose the method as defined in any of the above, wherein said step of incubating is been performed at a temperature of 25-37° c. for 6-24 hours; said incubating is been performed with 5-6% $CO_2$.

It is another object of the present invention to disclose a method for producing autologous IL-1RA cytokine in a closed system, the method comprising the steps of:

a. obtaining a syringe system for producing autologous IL-1RA cytokine comprising:
 i. a blood collection syringe;
 ii. an anticoagulant portion;
 iii. a syringe stopper;
 iv. a sharp syringe needle; and
 v. an incubation vessel with a cover comprising washed and pretreated borosilicate glass beads in a size of about 0.5-5 mm;
b. placing the anticoagulant portion in the blood collection syringe;
c. drawing whole blood with said blood collection syringe;
d. positioning said syringe in an downward position comprising a stopper;
e. separating said whole blood in said syringe by centrifugation yielding separation fractions comprising, a first fraction of RBCs sediment, a second fraction comprising WBCs, platelets and, and a third fraction of plasma solution;
f. discarding RBCs fraction from said syringe;
g. transferring the fraction of WBCs, platelets, growth factors and portion of plasma solution into incubation vessel; and
h. incubating said incubation vessel;
such that a high concentration of said autologous IL-1RA cytokine is obtained.

It is another object of the present invention to disclose the method as defined in any of the above, wherein at least one of the following holds true:
 a. providing said anticoagulant selected from the group consisting of: a citrate-based anticoagulant, EDTA salt, heparin salt-based anticoagulant, oxalate-based anticoagulant and any combination thereof; and
 b. selecting said incubation vessel from the group consisting of: plastic tube, glass tube and any combination thereof.

It is another object of the present invention to disclose the method as defined in any of the above, wherein at least one of the following holds true:
 a. said incubating is been performed at a temperature of 25-37° C. for 6-24 hours;
 b. said incubating is been performed with or without 5-6% $CO_2$;
 c. performing said centrifugation for about 10 to about 30 minutes; and
 d. transferring portion of plasma to said incubation vessel is up to 5%.

It is another object of the present invention to disclose a method for producing of autologous IL-1RA cytokine in a closed vessel tube system, the method comprising the steps of:
a. obtaining a vessel system for producing autologous IL-1RA cytokine comprising:
 i) an incubation vessel comprising an anticoagulant portion and washed and pretreated borosilicate glass beads in a size of about 0.5-5 mm for collection blood sample; and,
 ii) a vessel cover;
b. filling said incubation vessel with whole blood sample; and
c. incubating said incubation vessel;
such that higher concentration of said autologous IL-1RA cytokine is formed.

It is another object of the present invention to disclose the method as defined in any of the above, wherein said step of incubating is being performed at a temperature of 25-37° c. for 6-24 hours; said incubating being performed with 5-6% CO.

It is another object of the present invention to disclose the method as defined in any of the above, wherein at least one of the following holds true:
  a. selecting said anticoagulant portion from the group consisting of: a citrate-based anticoagulant, EDTA salt, heparin salt-based anticoagulant, oxalate based anticoagulant and any combination thereof; and
  b. selecting said incubation vessel from the group consisting of: a plastic tube, a glass tube, a vacuum tube and any combination thereof.

BRIEF DESCRIPTION OF THE INVENTION

In order to understand the invention and to see how it may be implemented in practice, a few preferred embodiments will now be described, by way of non-limiting example only, with reference to be accompanying drawings, in which:

FIG. 1 presents a closed system for derivation of high levels of autologous IL-1RA cytokine in WBCs enriched plasma, in accordance with a preferred embodiment of the present invention; and, FIG. 2 presents a closed syringe system for derivation of high levels of autologous IL-1RA cytokine, in accordance with a preferred embodiment of the present invention; and, FIG. 3 presents a closed vessel system for derivation of high levels of autologous IL-1RA cytokine, in accordance with a preferred embodiment of the present invention; and, FIG. 4 presents a closed vessel system for derivation of high levels of autologous IL-1RA cytokine, in accordance with a preferred embodiment of the present invention;

FIG. 5 presents a closed vessel system for derivation of high levels of autologous IL-1RA cytokine in a whole blood sample, in accordance with a preferred embodiment of the present invention;

DETAILED DESCRIPTION

The following description is provided so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide methods and systems for producing high levels of autologous IL-1RA cytokine.

The term "Buffy coat collection syringe" is used herein to denote a second syringe which is used for collecting the fraction comprising WBCs and platelets with or without the remaining plasma.

As used herein the term "about X" or "approximately X" or "substantially X" usually refers to a range 25% less than to 25% more than of X (X±25%), at times X±20%, X±15% and preferably X±10%.

Figure 1:
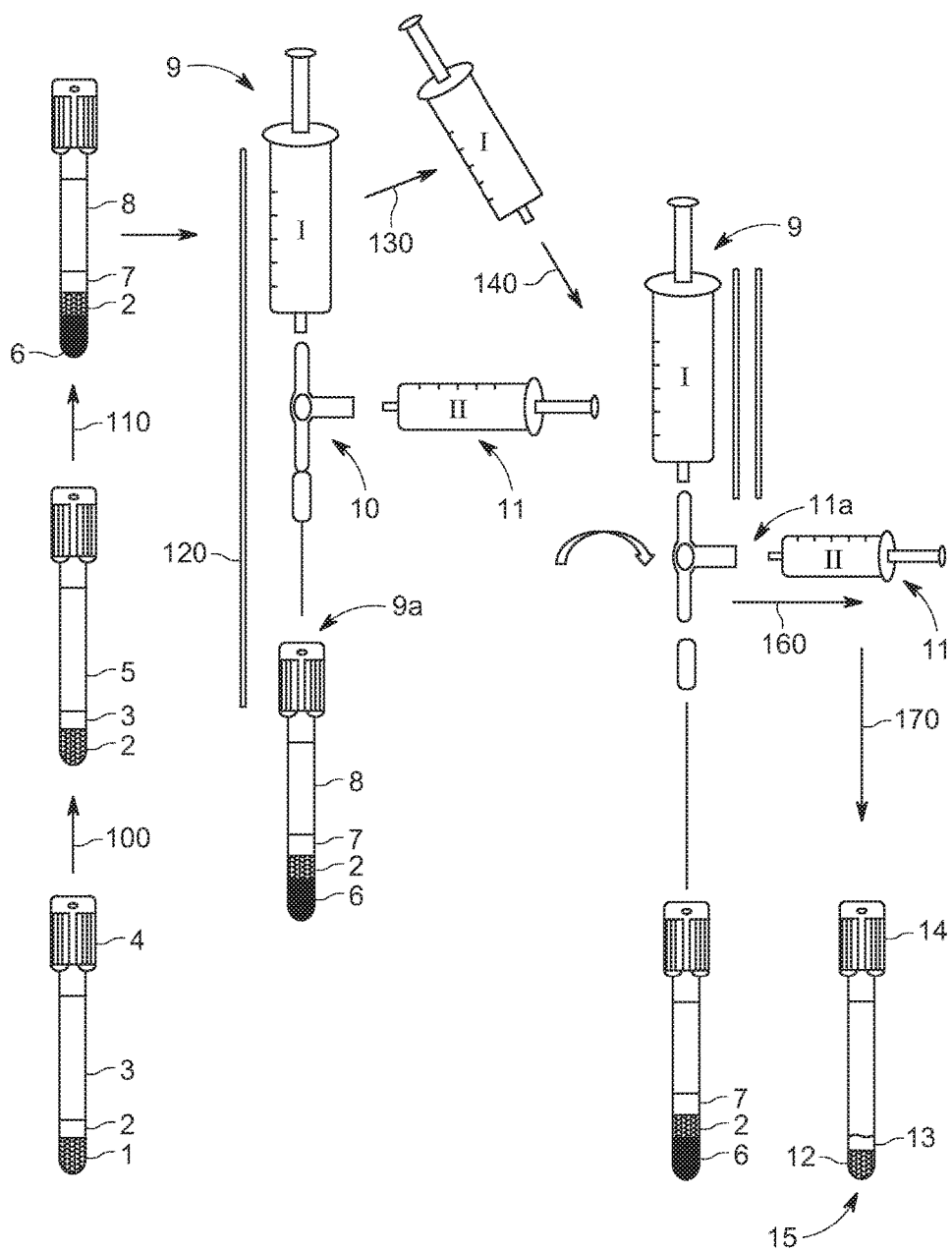

Reference is now made to FIG. 1 which illustrates a closed system for deriving high levels of autologous IL-1RA cytokine in WBCs enriched plasma.

In accordance with the preferred embodiment of the present invention all the elements of the invention such as tubes, syringes etc are combined in a closed system.

The closed system for producing autologous IL-1RA cytokine comprises: (a) a vacuum tube (1) adapted for collecting a blood sample (5), (b) a cover for the tube (4), (c) a separation gel layer (2), (d) an anticoagulant (3), (e) (f) a plasma portion collection syringe (9) comprising a sharp needle (9a) and an optional filter unit, (g) a buffy coat collection syringe (11), and (h) a tube for incubation (15) with a cover.

In some embodiments, test tubes are made of glass or MPA (modified poly Amide) or modified PET (Poly Ethylene Terephtalate). In some embodiments, the test tube has a layered structure such that the interior wall of the test tube comprises polypropylene. Test tubes can further be provided with a special cover. By way of non-limiting example the cover is made of butyl rubber or its halo derivative formulations at hardness between 40-60 Shore A. The hardness assures stable vacuum for at least the shelf life of the test tube which can be between 18-24 months.

The test tubes used can be of various sizes which depend of the required quantity of whole blood to be drawn from the treated subject. The test tubes have typically a size suitable for blood samples in the range of 4 ml to 100 ml.

The incubation tube is selected from the group consisting of: plastic tube, glass tube, or any combination thereof. The equipment consisting of a plastic hub, a hypodermic needle, and a vacuum tube. Under certain circumstances, a syringe may be used, often with a butterfly needle, which is a plastic catheter attached to a short needle. In the developing world, a needle and syringe are still the most common method of drawing blood.

In accordance with the preferred embodiment of the present invention, FIG. 1 shows the vacuum tube (1) consisting of a separation gel layer (2) at a density of about 1.06-1.09 gr/cm$^3$ and more preferably of about 1.08-1.09 gr/cm$^3$ and an anticoagulant layer (3). The anticoagulant is selected from the group consisting of: a citrate-based anticoagulant, EDTA salt, heparin salt-based anticoagulant, oxalate based anticoagulant, or any type of anticoagulant designed for preventing clotting of blood.

A blood sample (100) is drawn from a subject to the blood collection tube which comprises the gel layer (2) and the anticoagulant layer (3). In order to perform a separation of whole blood (5) a centrifugation procedure (110) is performed at (300)-1500 g for about 10 to about 30 minutes, resulting in four fractions. The first and heaviest fraction at the bottom of the tube comprises red blood cells (RBCs) layer 6 as a sediment layer, the second fraction comprises the gel layer (2), the third fraction, a buffy coat fraction, on the top of the gel, comprises: white blood cells (WBCs), platelets, and growth factors as a thin layer (7), and the last (fourth) fraction comprises plasma solution (8) as a supernatant layer.

The test tubes, in some embodiments, can contain an anticoagulant such as, but not limited to buffer citrate, modified ACD (citric/citrate dextrose), heparinate salts, EDTA salts, iodo acetate salts, oxalate salts, fluoride salts as water solutions or lyophilized material or wet or dry spray on inner wall and so forth.

While the test tube may optionally include an anti-coagulant, in some procedures an anti-coagulant may a priori not be included. For example, if the blood sample is withdrawn and maintained in cold conditions, an anti-coagulant may not be needed. In addition, in some procedures, the anti-coagulant may be mixed with the whole blood which was withdrawn from a subject, prior to inserting the whole blood into the tube.

In some embodiments of the invention no gel will be used. Thus, the components of this embodiment of the invention are vacuum tube (1) containing anticoagulant (3). This tube when contains whole blood sample is centrifuged at 300-1500 g for about 10 to about 30 minutes, resulting in three fractions; namely the first and heaviest fraction at the bottom of the tube comprises red blood cells (RBCs) layer (6) as a sediment layer, the second fraction, a buffy coat fraction, on the top of the gel, comprises: white blood cells (WBCs), platelets as thin layer (7), and the third fraction comprises plasma solution (8) as a supernatant layer. In yet another embodiment of the invention no anticoagulant will be used, the blood collection tube containing separation gel layer and whole blood sample will be centrifuged, resulting in four fractions: the first and heaviest fraction at the bottom of the tube comprises red blood cells (RBCs) layer 6 as a sediment layer, the second fraction comprises the gel layer (2), the third fraction comprises a buffy coat fraction, on the top of the gel. The buffy coat fraction comprises: white blood cells (WBCs), platelets, and growth factors as thin layer (7), and the last fraction comprises plasma solution (8) as a supernatant layer. In both cases, (with or without gel), after centrifugation (110) a portion of plasma (8) is discarded (120) from the tube using a syringe (9) with a sharp needle (9a).

In some embodiments of the invention the amount of plasma (8) which extracted from the blood collection tube (1) is up to 80% of plasma. In another embodiment of the invention, the amount of plasma (8) which extracted from the tube (1) is at least 50% of plasma. In yet another embodiment of the invention the amount of plasma which extracted from the tube (1) is about 80% of plasma.

Extraction of the plasma (120) and re-suspending of WBCs, platelets and growth factors is performed via repeated pumping of the plasma solution using a plasma collection syringe and an optional stopcock (10) as a valve or turning plug which controls the flow of fluid from a the plasma collection syringe to the blood collection tube. A higher potency of the IL-1RA is obtained when plasma portion containing IL-1RI molecules which may bind and inhibit IL-1RA, is discarded.

In another embodiment of the invention a two or three-way stopcock can be used to turn off the flow of one solution and turn on the flow of another.

In another embodiment of the invention, the plasma collection syringe (9) may also include a filter unit of having pores size of about 0.2-50 µm anf more preferably of about 3-50 µm, attached to the long sharp needle 9a for piercing the stopper (10). The remaining amount of the top fraction comprising; plasma (8), and the fraction comprising WBCs and platelets (7) are drawn using a buffy coat collection syringe (11), attached to the hub of the long sharp needle or via attaching a syringe to another port of the stopcock (10) with an optional filter unit.

In another embodiment of the invention an optional stopcock (10) as a valve or turning plug controls the flow of fluid from the buffy coat collection syringe to the blood collection tube. In another embodiment of the invention a two or three-way stopcock can be used also to turn off the flow of one solution and turn on the flow of another. The plasma layer, and WBCs layer in the buffy coat collection syringe (11) are transferred to an incubation tube (15) closed with a cover (14). The incubation tube comprises washed and pretreated borosilicate glass beads (12) in size of about 0.5-5 mm. An incubation is carried out on the incubation tube at temperature of 25-37° c. with optional addition of $CO_2$ for 6-24 hours producing high levels of the autologous IL-1RA cytokine.

Figure 2:
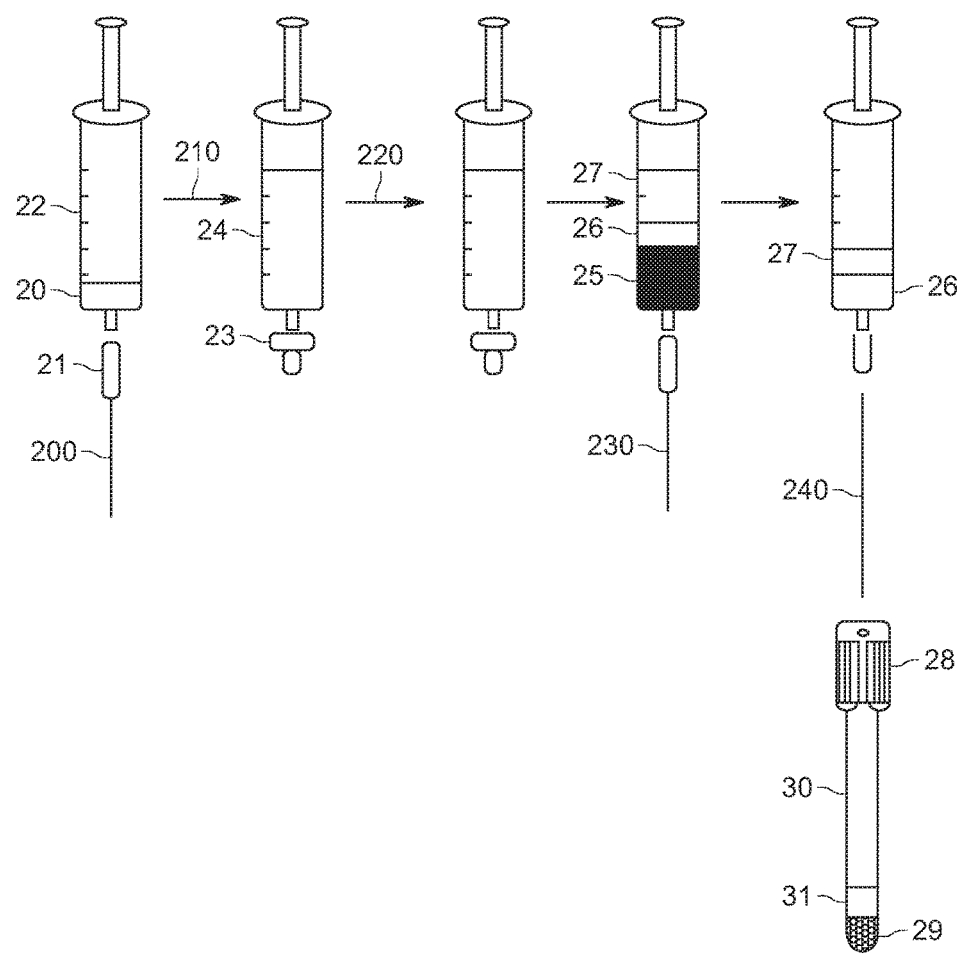

Reference is now made to FIG. 2 which illustrates a closed syringe system for deriving high levels of autologous IL-1RA cytokine. The syringe system for producing autologous IL-1RA cytokine comprises: (a) a blood collection syringe (22), (b) an anticoagulant portion, (c) a syringe stopper (23), (d) a syringe sharp needle (21), and (e) an incubation vessel with a cover (30). The vessel is selected from a group consisting of: a syringe, a plastic tube, a glass tube, or any other suitable vessel.

Whole blood is drawn (200) from a subject using a blood collection syringe (22) having an anticoagulant layer (21). The anticoagulant is selected from the group consisting of: a citrate based anticoagulant, EDTA salt, heparin salt based anticoagulant, oxalate based anticoagulant, or any type of anticoagulant designed for preventing clotting of blood. The syringe (22) closed (210) with a stopper (23), is centrifuged (220) in a downward position at 300-1500 gr for about 10 to about 30 minutes resulting in three fractions. The first and heaviest fraction comprises RBCs sediment (25) in the bottom of the syringe (22), upon it, the second fraction, buffy coat fraction comprises, WBCs, platelets and growth factors layer (26), and the third fraction comprises a plasma solution (27) as a supernatant layer. The RBCs layer (25) is discarded (230) from the blood collection syringe by removing the stopper (23) and pressing the plunger of the blood collection syringe. The remaining fractions comprise; a first fraction of WBCs sediment (26) and a second fraction of the plasma solution (27). The fraction of WBCs (26) and about 5% to about 100% of the plasma solution (27) are transferred to a vessel (240) suitable for incubation (30) with washed and pretreated borosilicate glass beads (29) of size of about 0.5-5 mm. An incubation of the vessel is carried out at temperature of 25-37° c. with optional addition of $CO_2$ for 6-24 hours producing high levels of the autologous IL-1RA cytokine.

In accordance with the preferred embodiment of the present invention, the incubation vessel is selected from the group consisting of: plastic tube, glass tube, or any combination thereof.

Figure 3:
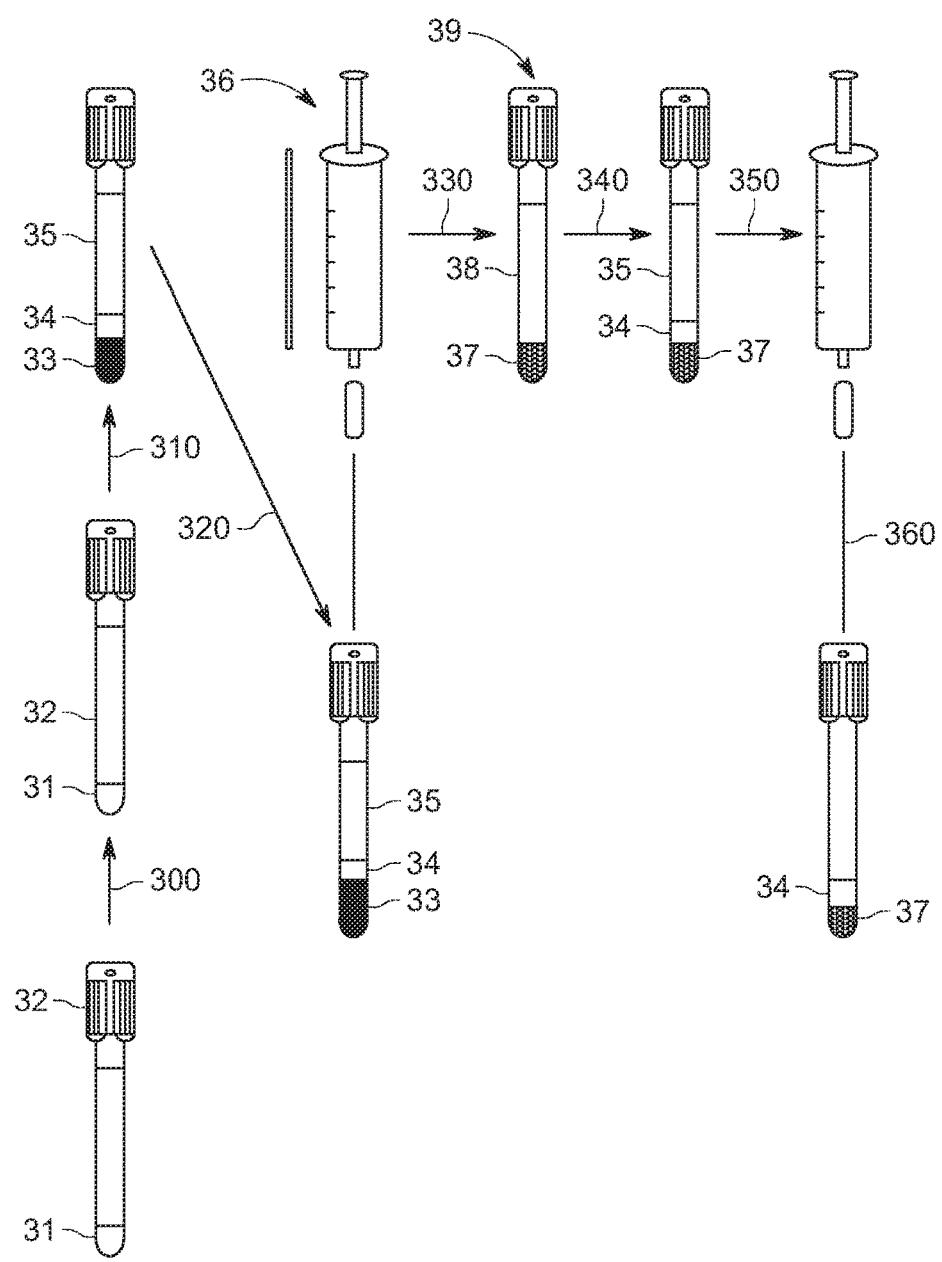

Reference is now made to FIG. 3 which illustrates a closed vessel system for derivation of high levels of autologous IL-1RA cytokine via a gravitation method. FIG. 3 illustrates a vessel system for producing autologous IL-1RA cytokine comprising (i) a blood collection vessel (30), (ii) a vessel cover, (iii) an anticoagulant (31), (iv) a plasma and WBCs portion collection syringe comprising a sharp long needle, (v) an incubation vessel with a cover (39), and (v) a plasma portion collection syringe.

In another embodiment of the invention, he blood collection vessel is selected from a group consisting of: a plastic tube, a glass tube, a vacuum tube or any other suitable vessel.

In some embodiments of the invention a blood sample (32) is drawn 300 from a subject to the blood collection vessel (30), closed with a cover (32) and positioned in an upward position (310) for 20-60 min. Gravity causes the precipitation of RBCs, thereby resulting in three fractions. The first fraction in the bottom of the vessel comprises: a sediment of RBCs layer (33), the second fraction comprises WBCs, platelets (34) on top of the RBCs layer and the third fraction comprises a plasma solution (35) as a supernatant layer. The WBCs layer and the plasma layer are transferred (320) to an incubation vessel (39) via a plasma and WBCs portion collection syringe. Centrifugation (340) of the incubation vessel (39) comprising washed and pretreated borosilicate glass beads (29) of size of about 0.5-5 mm is performed at 200-1500 g for about 10 to about 30 minutes, resulting in three fractions. The first fraction in the bottom of the vessel comprises the glass beads (37), upon it, the second fraction, a buffy coat fraction, comprising WBCs, platelets, growth factors (34), and the third fraction comprises the plasma solution (35).

In yet another embodiment of the invention, after centrifugation (340) a portion of plasma (35) is discarded from the incubation tube using a plasma collection syringe with a sharp needle.

In some embodiments of the invention the amount of plasma (8) which extracted from the blood collection tube 1 is up to 80% of the plasma. In another embodiment of the invention, the amount of plasma (8) which extracted from the tube 1 is at least 50% of the plasma. The incubation vessel (39) containing the glass beads (37), and a fraction of a buffy coat fraction, comprising WBCs, platelets, growth factors (34), is incubated at 25-37° c. with optional addition of $CO_2$ for 6-24 h, to produce high levels of the autologous IL-1RA cytokine.

In another embodiment of the invention, the buffy coat fraction comprising: WBCs, platelets and growth factors and the plasma fraction. Those fractions are transferred from the blood collection vessel to the centrifugation vessel via a plasma and WBCs portion collection syringe. Centrifugation at 200-1500 g for about 10 to about 30 minutes in the centrifugation vessel results in two separate fractions comprising: first fraction of WBCs and second fraction of plasma.

A portion of the plasma is discarded using a plasma collection syringe and the WBCs and the remaining plasma are transferred to an incubation vessel which comprises washed and pretreated borosilicate glass beads in size of about 0.5-5 mm. In another embodiment of the invention the amount of plasma which extracted from the tube is up to 80% of the plasma.

In another embodiment of the invention the amount of plasma which extracted from the tube is at least 50% of the plasma. In another embodiment of the invention the amount of plasma which extracted from the tube is about 80% of the plasma.

In accordance of the invention, the incubation vessel is incubated at 25-37° c. with an optional addition of $CO_2$ for 6-24 h, to produce high levels of the autologous IL-1RA cytokine.

In another embodiment of the invention the incubation vessel is selected from a group consisting of: a plastic tube, a glass tube, or any other suitable vessel.

Figure 4:
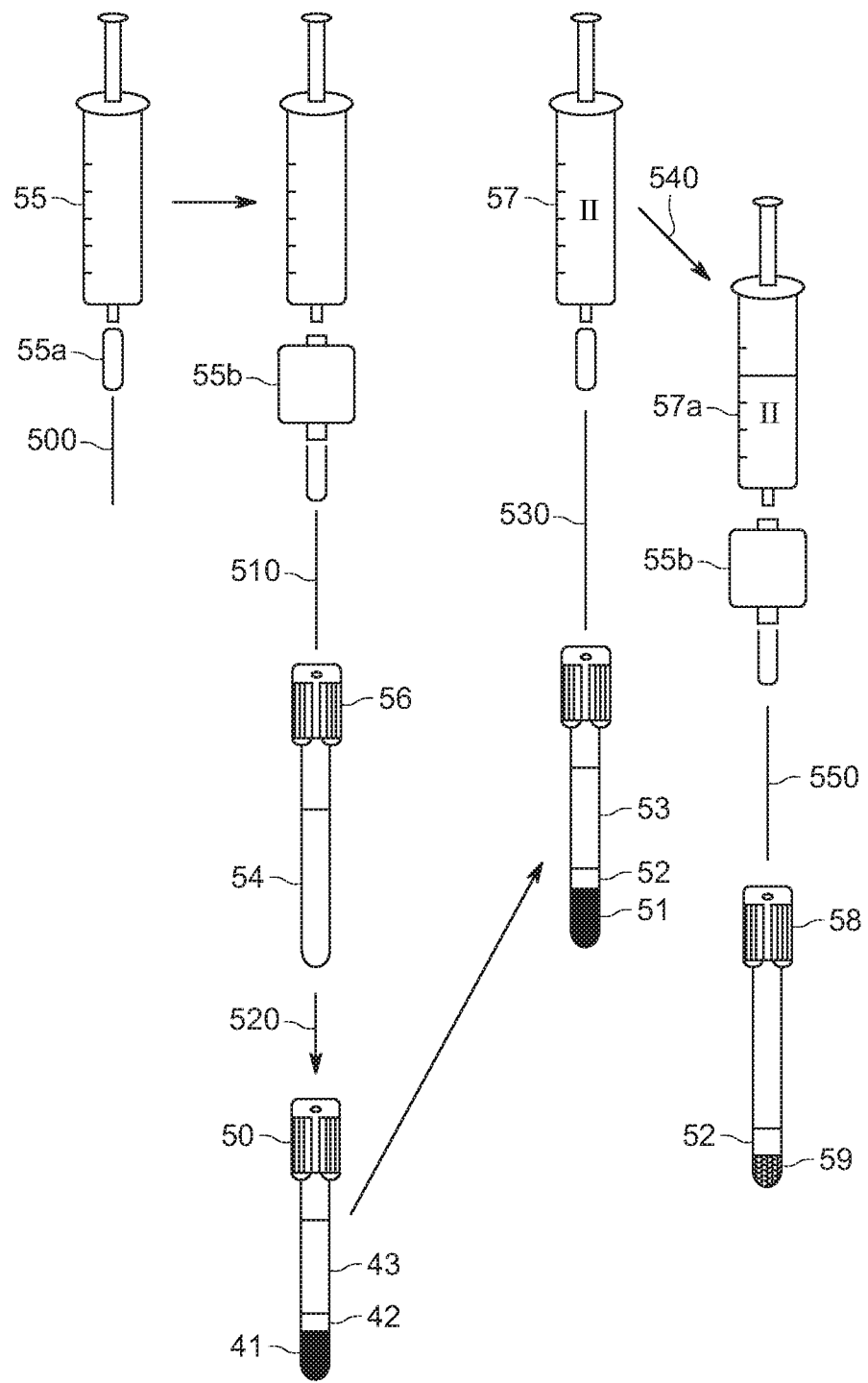

Reference is now made to FIG. 4 which illustrates a closed system for derivation of high levels of autologous IL-1RA cytokine via filtration. FIG. 4 shows a vessel system for producing autologous IL-1RA cytokine comprising: (a) a filtered blood sample tube (50); (b) a tube cover, (c) a blood collection syringe (55) comprising a sharp needle (55a) and a filter unit (55b), (d) an incubation vessel with a cover (58), and (e) a plasma portion collection syringe (57) with a sharp needle (57a).

In another embodiment of the invention, the tube is selected from a group consisting of: a plastic tube, a glass tube, a vacuum tube or any other suitable vessel.

In accordance with the preferred embodiment of the present invention, the whole blood sample is drawn (500) from a subject, using a blood collection syringe (55). The whole blood sample is passed (510) through a special filter (55b) such as hydrophilic filter or hydrophobic filter. The filter includes multi-sized pores which captures nucleated cells as WBCs, while letting the RBCs and the plasma flow through to a filtered blood sample tube. The filtered blood sample tube (50) is centrifuged (520) at 300-1500 g for about 10 to about 30 minutes to obtain cell free plasma, resulting in three fraction. The first and heaviest fraction at the bottom of the vessel comprises RBCs sediment (51), the second fraction comprises platelets (52), and the third fraction comprises plasma solution (53) as a supernatant layer. The plasma layer is drawn (530) by a plasma portion collection syringe (57). The next step is performing a flushing (550) by attaching the filter (540) consisting of the captured WBCs fraction (55b) to the plasma portion collection syringe (57) consisting of the plasma (57a). The flushing obtains and release the WBCs to an incubation vessel with a cover 58 which contains washed and pretreated borosilicate glass beads (59) in size of about 0.5-5 mm. The incubation vessel containing the WBCs fraction (58) is then incubated at 25-37° C. with optional addition of $CO_2$ for 6-24 h, to produce high levels of the autologous IL-1RA cytokine.

Figure 5:
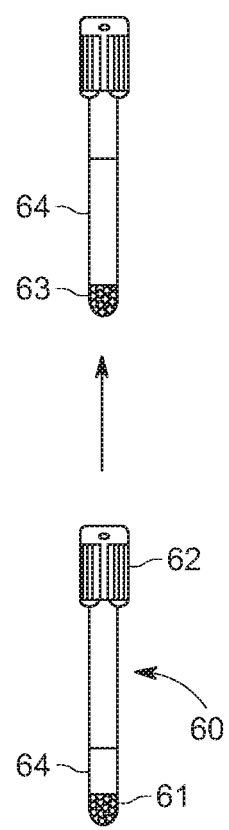

In another embodiment of the invention the incubation vessel is selected from a group consisting of: a plastic tube, a glass tube, or any other suitable vessel Reference is now made to FIG. 5 which illustrates a closed system for derivation of high levels of autologous IL-1RA cytokine in a whole blood sample.

FIG. 5 shows an incubation vessel (60) with a cover (62) for producing autologous IL-1RA cytokine. The vessel comprises washed and pretreated borosilicate glass beads (61) in size of about 0.5-5 mm and may also comprises an anticoagulant layer. The incubation vessel is selected from a group consisting of: a syringe, a plastic tube, a glass tube, a vacuum tube or any other suitable vessel. The anticoagulant is selected from the group consisting of: a citrate-based anticoagulant, EDTA salt, heparin salt based anticoagulant, oxalate based anticoagulant, or any type of anticoagulant designed for preventing clotting of blood. A whole blood sample (64) is drawn to the incubation vessel (60) and incubated at 25-37° C. with optional addition of $CO_2$ for 6-24 hours, to produce high levels of the autologous IL-1RA cytokine.

Figure 6:
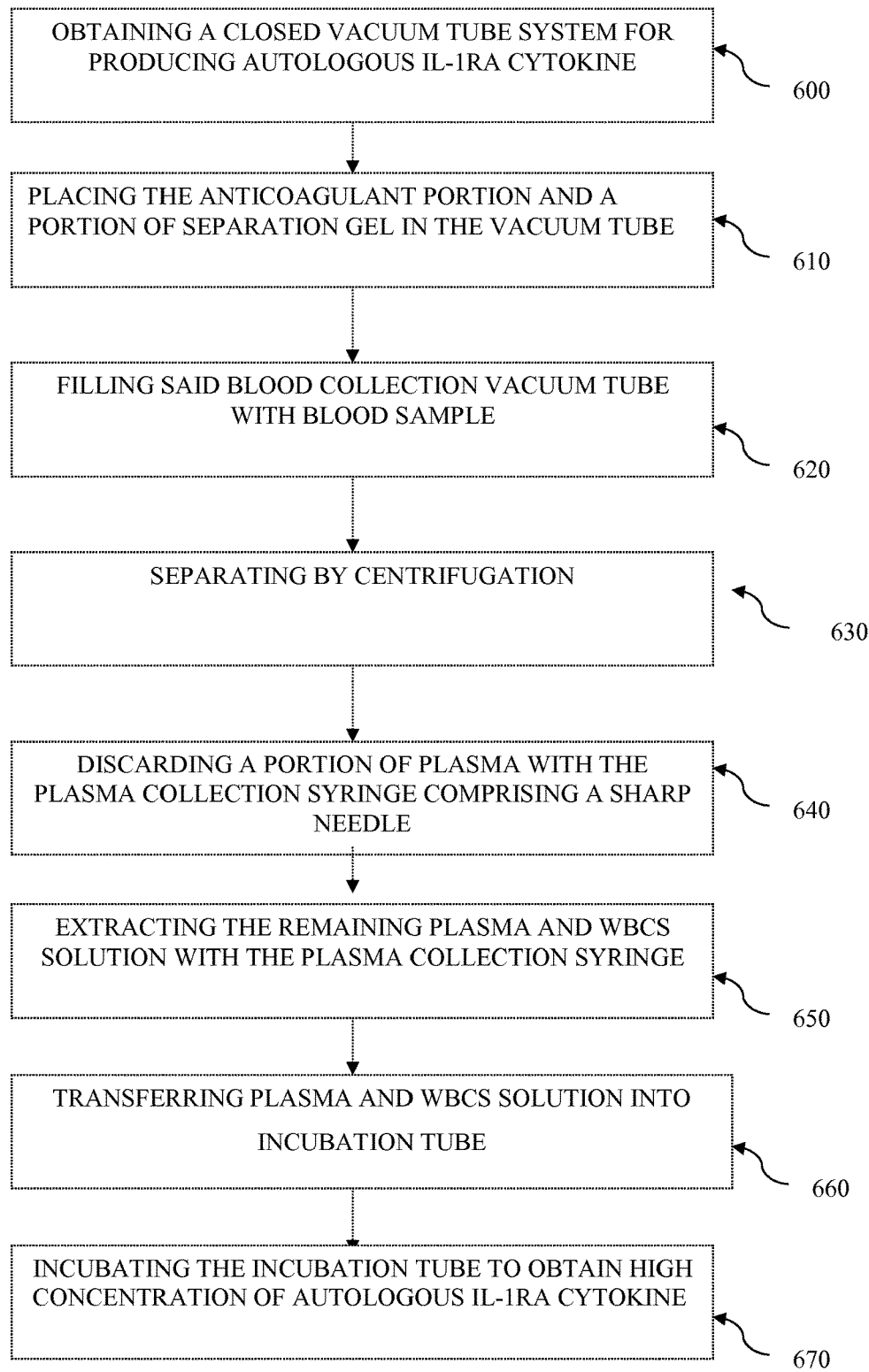
FIG. 6 illustrates a flow chart of a method for producing of autologous IL-1RA cytokine in a closed system, in accordance with a preferred embodiment of the present invention.

Reference is now made to FIG. 6 which illustrates a flow chart of the method for producing of autologous IL-1RA cytokine in a closed system, the method comprising steps of: (a) obtaining a vacuum tube system for producing autologous IL-1RA cytokine (600) comprising: (i) a blood collection vacuum tube; (ii) a tube cover; (iii) a portion of separation gel;

(iv) an anticoagulant portion; (v) a plasma collection syringe comprising a sharp needle; (vi) a portion collection syringe; and (vii) an incubation tube with a cover;
(b) placing the anticoagulant portion and the portion of separation gel in the vacuum tube (610), (c) filling the blood collection vacuum tube with blood sample (620), (d) separating by centrifugation yielding four separation fractions. The first fraction comprises RBCs sediment, the second fraction comprising the gel, a third fraction comprises WBCs, platelets and, and fourth fraction comprises plasma solution (630), (e) discarding a portion of plasma with the plasma collection syringe comprising a sharp needle (640), (f) extracting the remaining plasma and WBCs solution with the plasma collection syringe (650), (g) transferring the solution into incubation tube (660), and (h) incubating the incubation tube; such that a high concentration of the autologous IL-1RA cytokine is obtained (670).

In another embodiment of the invention the method as described above, wherein the incubation tube comprises washed and pretreated borosilicate glass beads in a size of about 0.5-5 mm. In another embodiment of the invention the method as described above, further comprises a filter unit having pore size of about 0.2-50 μm or preferably of about 3-50 μm.

In another embodiment of the invention the method as described above, wherein the incubation tube is selected from the group consisting of: a plastic tube, a glass tube, or any combination thereof. In another embodiment of the invention the method as described above, wherein the separation gel is at density of about 1.06-1.09 gr/cm$^3$ or more preferably of about 1.08-1.09 gr/cm$^3$.

In another embodiment of the invention, the method as described above comprises discarding up to 80% of plasma from the blood collection vacuum tube.

In another embodiment of the invention, the method as described above comprises discarding at least 50% of plasma from the blood collection vacuum tube.

In another embodiment of the invention, the method as described above comprises discarding about 80% of plasma from the blood collection vacuum tube.

In another embodiment of the invention, the method as described above comprises using an anticoagulant selected from the group consisting of: a citrate based anticoagulant, EDTA salt, heparin salt based anticoagulant, oxalate based anticoagulant, or any combination thereof. In another embodiment of the invention the method as described above, wherein the anticoagulant comprises any type of anticoagulant designed for preventing clotting of blood.

In another embodiment of the invention, the method as described above, wherein the incubating is been performed at temperature of 25-37° c. for 6-24 hours. In another embodiment of the invention the method as described above, wherein the incubating is being performed with or without 5-6% $CO_2$.

Figure 7:
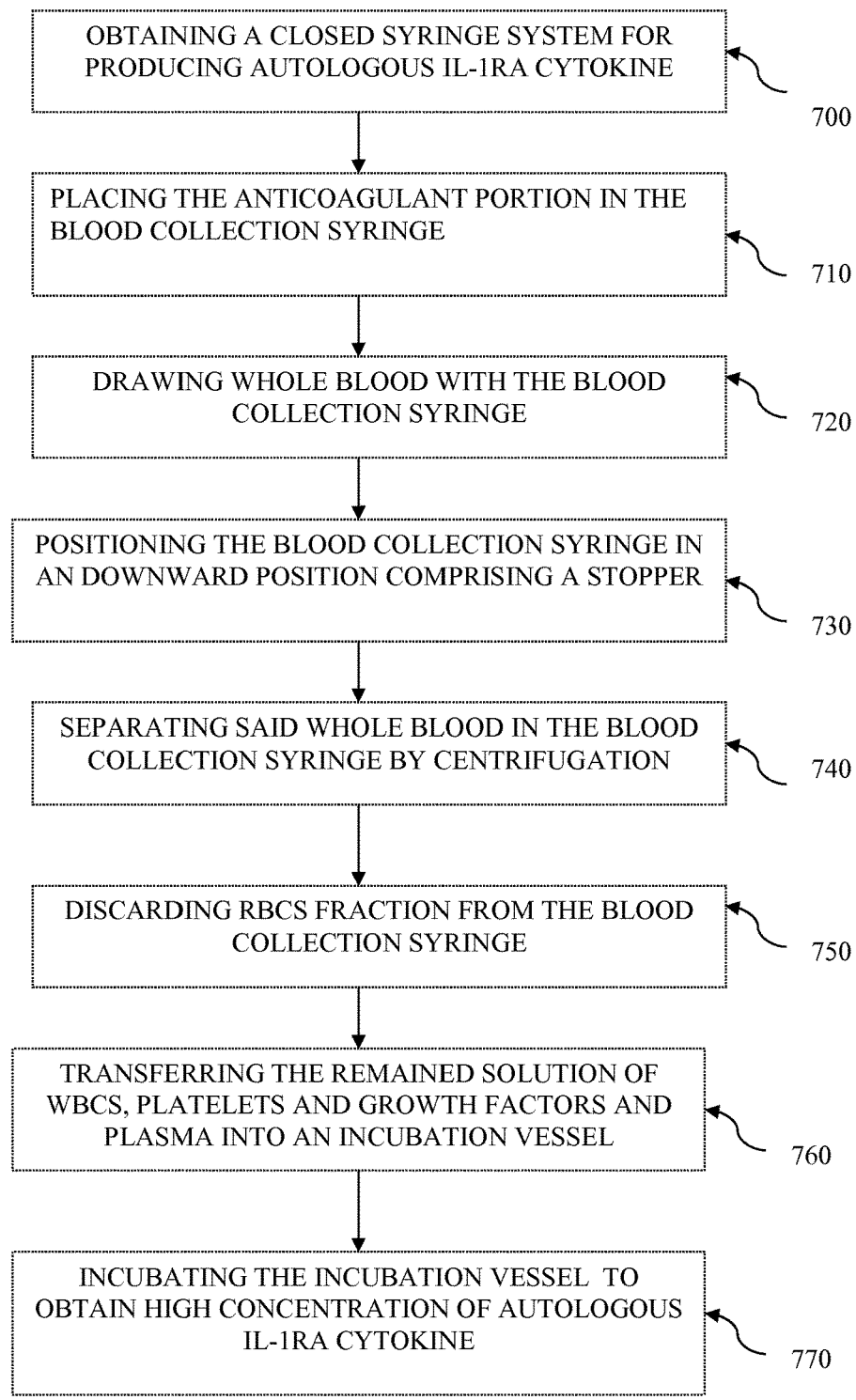
FIG. 7 illustrates a flow chart of a method for producing of autologous IL-1RA cytokine in a closed syringe system, in accordance with a preferred embodiment of the present invention.

Reference is now made to FIG. 7 which illustrates a flow chart of the method for producing autologous IL-1RA cytokine in a closed system, the method comprising the steps of: (a) obtaining a syringe system for producing autologous IL-1RA cytokine (700) comprising:
(i) a blood collection syringe; (ii) an anticoagulant portion; (iii) a syringe stopper; (iv) a sharp syringe needle; and, (v) an incubation vessel with a cover;
(b) placing the anticoagulant portion and the portion of separation gel in the blood collection syringe (710); (c) drawing whole blood with the blood collection syringe (720), (d) positioning the syringe in an downward position comprising a stopper (730), (e) separating the whole blood in the syringe by centrifugation yielding separation fractions comprising, a first fraction of RBCs sediment, a second fraction comprising WBCs, platelets and a third fraction of plasma solution (740), (f) discarding RBCs fraction from the syringe (750), (g)transferring the remained solution of WBCs, platelets and growth factors into incubation vessel (760), and (h) incubating the incubation vessel such that a high concentration of the autologous IL-1RA cytokine is obtained (770).

In another embodiment of the invention the method as described above, wherein the anticoagulant is selected from the group consisting of: a citrate based anticoagulant, EDTA salt, heparin salt based anticoagulant, oxalate based anticoagulant, or any combination thereof.

In another embodiment of the invention the method as described above, wherein the anticoagulant comprises any type of anticoagulant designed for preventing clotting of blood.

In another embodiment of the invention the method as described above, wherein the incubation vessel contains pretreated and washed borosilicate glass beads in a size of about 0.5-5 mm In another embodiment of the invention the method as described above, wherein the incubating is being performed at temperature of 25-37° c. for 6-24 hours.

In another embodiment of the invention the method as described above, wherein the incubating is been performed with or without 5-6% $CO_2$.

In another embodiment of the invention the method as described above, wherein the incubation vessel is selected from the group consisting of: plastic tube, glass tube, or any combination thereof.

In another embodiment of the invention the method as described above, wherein the centrifugation is been performed for about 10 to about 30 minutes.

Figure 8:
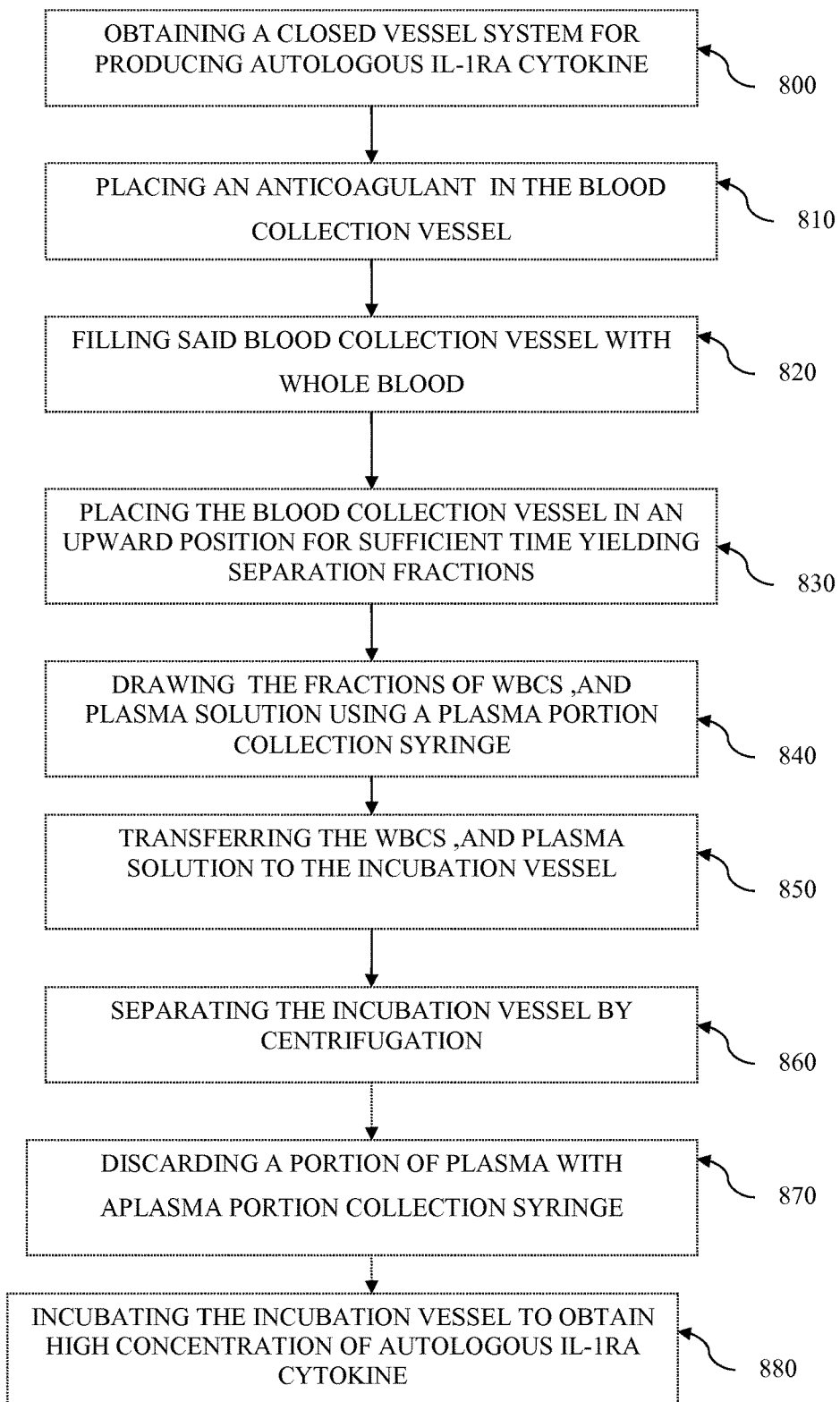
FIG. 8 illustrates a flow chart of a method for producing of autologous IL-1RA cytokine in a closed vessel system, in accordance with a preferred embodiment of the present invention.

Reference is now made to FIG. 8 which illustrates a flow chart of the method for producing of autologous IL-1RA cytokine in a closed vessel system, the method comprising the steps of: (a) obtaining a vessel system for producing autologous IL-1RA cytokine (800) comprising:
(i) a blood collection vessel, (ii) a vessel cover, (iii) an anticoagulant, (iv) a plasma portion collection syringe comprising a sharp needle, (v) an incubation vessel with a cover; and (vi) a buffy coat collection syringe.
(b) placing the anticoagulant in the blood collection vessel (810), (c) filling the blood collection vessel with blood (820), (d) placing the vessel in an upward position for sufficient time yielding separation fractions comprising a first fraction of RBC sediment, and a second fraction comprising WBCs, platelets and a third fraction of plasma solution (830), (e) drawing the fractions of WBCs, and plasma solution using a plasma portion collection syringe (840), (f)transferring the WBCs, and plasma solution to the incubation vessel (850), (g) separating the incubation vessel by centrifugation, yielding separation fractions comprising a first fraction of WBCs sediment, and a second fraction of plasma solution (860), (h) discarding a portion of plasma with a collection syringe (870), (i) incubating the incubation vessel such that a high concentration of the autologous IL-1RA cytokine is obtained (880).

In another embodiment of the invention the method as described above, wherein the incubation vessel comprises washed and pretreated borosilicate glass beads in a size of about 0.5-5 mm.

In another embodiment of the invention the method as described above, wherein the anticoagulant is selected from the group consisting of: a citrate based anticoagulant, EDTA salt, heparin salt based anticoagulant, oxalate based anticoagulant, or any combination thereof.

In another embodiment of the invention, the method is performed as described above, and the anticoagulant comprises any type of anticoagulant designed for preventing clotting of blood. In another embodiment of the invention, the method is performed as described above, and the incubating is performed at a temperature of 25-37° C. for 6-24 hours.

In another embodiment of the invention, the method is performed as described above, wherein the incubating is performed with or without 5-6% $CO_2$.

In another embodiment of the invention, the method as described above includes discarding up to 80% of plasma from the incubation vessel.

In another embodiment of the invention, the method as described above includes discarding at least 50% of plasma from the incubation vessel.

In another embodiment of the invention, the method as described above includes discarding about 80% of plasma from the incubation vessel.

In another embodiment of the invention the method described above, the blood collection vessel is selected from the group consisting of: a syringe, a plastic tube, a glass tube, a vacuum tube and any combination thereof.

In another embodiment of the invention the method as described above, wherein the incubation vessel is selected from the group consisting of: a plastic tube, a glass tube, a syringe and any combination thereof. In another embodiment of the invention the method as described above, wherein the fraction of RBCs sediment is formed using gravity force. In another embodiment of the invention the method as described above, wherein the tube in upward position is positioned for about 20-60 minutes.

In another embodiment of the invention the method as described above, further comprises a filter unit having pores size of about 0.2-50 μm. In another embodiment of the invention the method as described above, wherein the centrifugation is being performed for about 10 to about 30 minutes.

Figure 9:
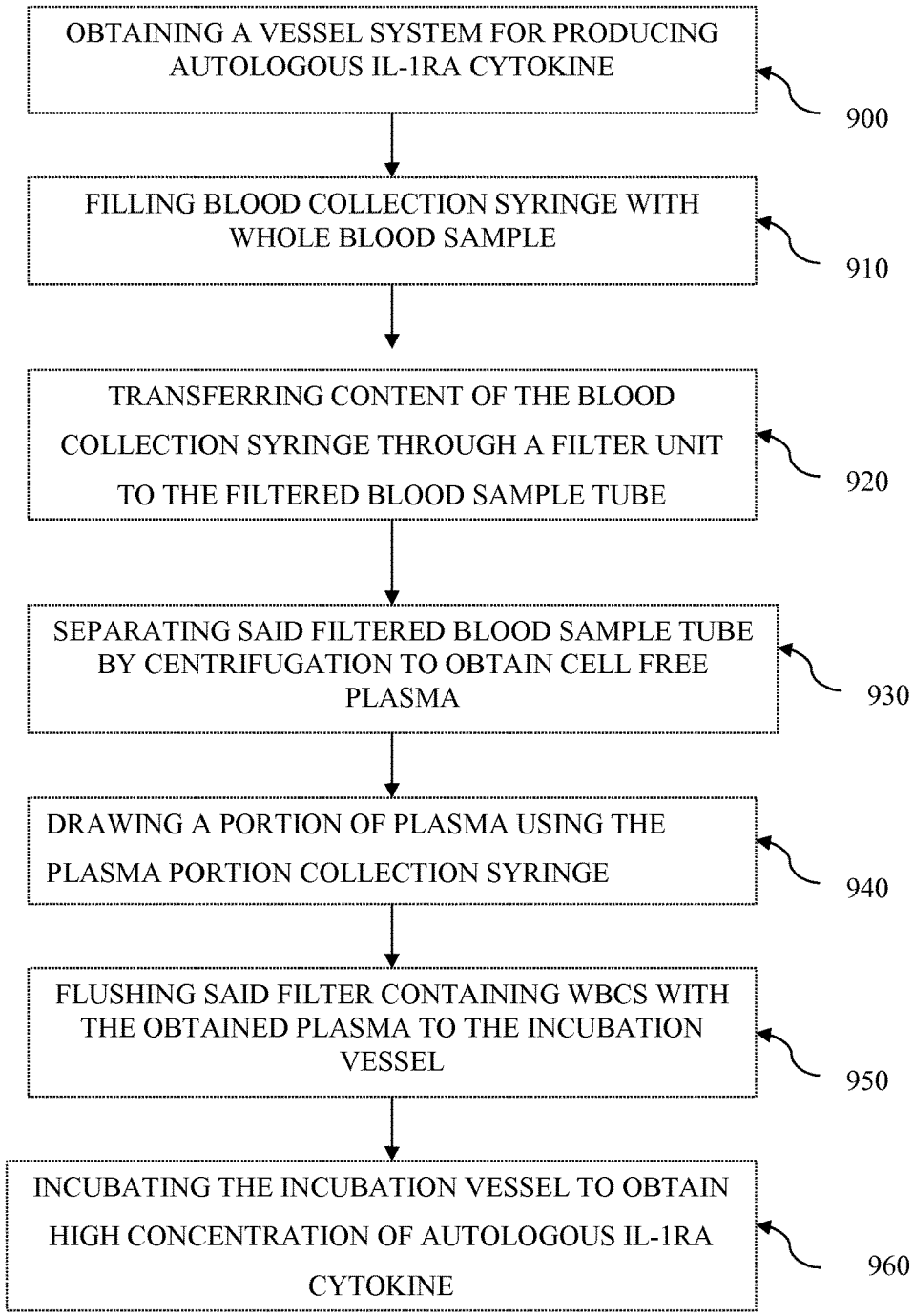
FIG. 9 illustrates a flow chart of a method for producing of autologous IL-1RA cytokine in a closed vessel system, in accordance with a preferred embodiment of the present invention.

Reference is now made to FIG. 9 which illustrates a flow chart of the method for producing of autologous IL-1RA cytokine in a closed vessel system, the method comprising the steps of: (a) obtaining a vessel system for producing autologous IL-1RA cytokine (900) comprising: (i) a blood collection syringe comprising a sharp needle and a filter unit, with blood sample; anticoagulant (ii) a filtered blood sample tube; (iii) a plasma portion collection syringe with a sharp needle; and (iv) an incubation vessel with a cover;
(b) filling syringe with whole blood sample (910), (c) transferring content of the syringe through a filter unit to the filtered blood sample tube (920), (d) separating the filtered blood sample tube by centrifugation yielding a separation fractions comprising a first fraction of RBCs sediment, a second fraction comprising, platelets and third fraction of plasma solution (930), (e) drawing a portion of plasma using the plasma portion collection syringe (940), (f) flushing the filter containing WBCs with the obtained plasma in the a plasma portion collection syringe to the incubation vessel yielding a WBCs fraction (950), (g) incubating the incubation vessel; such that a high concentration of the autologous IL-1RA cytokine is obtained (960).

In another embodiment of the invention the method as described above, wherein the incubation vessel contains pretreated and washed borosilicate glass beads in a size of about 0.5-5 mm.

In another embodiment of the invention the method as described above, wherein the step of drawing up to 80% of plasma from the filtered blood sample tube.

In another embodiment of the invention the method as described above, wherein the step of drawing at least 50% of plasma from the filtered blood sample tube.

In another embodiment of the invention the method as described above, wherein the step of drawing about 80% of plasma from the filtered blood sample tube.

In another embodiment of the invention the method as described above, wherein the filter unit is selected from the group consisting of: a hydrophobic filter, hydrophilic filter or any combination thereof.

In another embodiment of the invention the method as described above, wherein the incubating is being performed at temperature of 25-37° C. for 6-24 hours.

In another embodiment of the invention the method as described above, wherein the incubating is being performed with or without 5-6% $CO_2$.

In another embodiment of the invention the method as described above, wherein the filtered blood sample tube is centrifuged for about 10 to about 30 minutes.

In another embodiment of the invention the method as described above, wherein the filtered blood sample tube is selected from the group consisting of: a plastic tube, a glass tube, a vacuum tube or any combination thereof.

In another embodiment of the invention the method as described above, wherein the incubation vessel is selected from the group consisting of: a syringe, a plastic tube, a glass tube, or any combination thereof.

Figure 10:
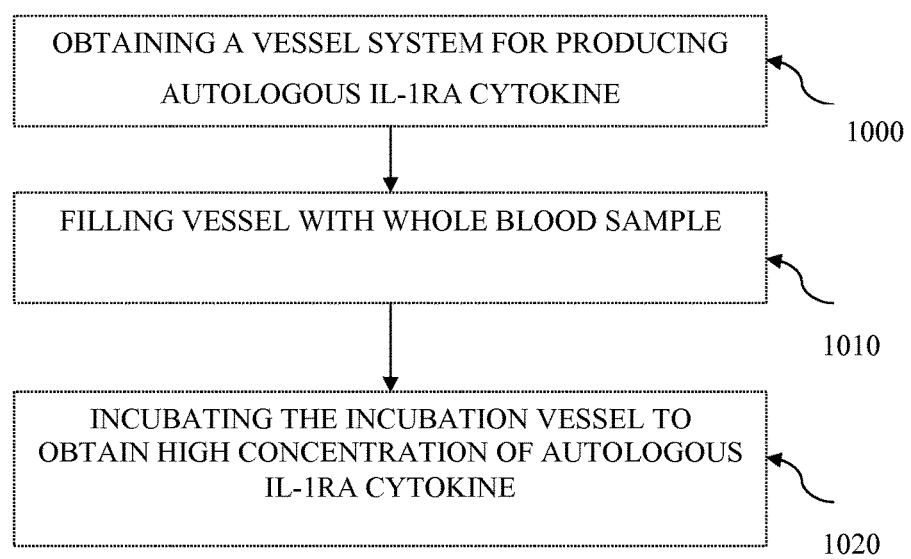
FIG. 10 illustrates a flow chart of a method for producing of autologous IL-1RA cytokine in a closed vessel system, in accordance with a preferred embodiment of the present invention.

Reference is now made to FIG. 10 which illustrates a flow chart of the method for producing of autologous IL-1RA cytokine in a closed vessel tube system, the method comprising the steps of: (a) obtaining a vessel system for producing autologous IL-1RA cytokine (1000) comprising: (i) an incubation vessel comprising washed and pretreated borosilicate glass beads for collection blood sample; (ii) a vessel cover;
(b) filling the incubation vessel with whole blood sample (1010), and (c) incubating the incubation vessel such that higher concentration of the autologous IL-1RA cytokine is formed (1020).

In another embodiment of the invention the method as described above, wherein the borosilicate glass beads are pretreated and washed beads in a size of about 0.5-5 mm In another embodiment of the invention the method as described above, wherein the incubating is been performed at temperature of 25-37° C. for 6-24 hours.

In another embodiment of the invention the method as described above, wherein the incubating is been performed with or without 5-6% $CO_2$.

In another embodiment of the invention the method as described above, further comprises an anticoagulant which is selected from the group consisting of: a citrate based anticoagulant, EDTA salt, heparin salt based anticoagulant, oxalate based anticoagulant, or any combination thereof.

In another embodiment of the invention the method as described above, wherein the anticoagulant comprises any type of anticoagulant designed for preventing clotting of blood.

In another embodiment of the invention the method as described above, wherein the filtered blood sample tube is centrifuged for about 10 to about 30 minutes.

In another embodiment of the invention the method as described above, wherein the incubation vessel is selected from the group consisting of: a plastic tube, a glass tube, a vacuum tube or any combination thereof.

It is known in the literature ("Differential binding of human interleukin-1 (IL-1) receptor antagonist to natural and recombinant soluble and cellular IL-1 type I receptors", Morten Svenson, Susanne Nedergaard, Peter M. H. Heegaard, Teri D. Whisenand, William P. Arend, Klaus Bendtzen. Eur. J. Immunol. 1995.25: 2842-2850) that IL-1RI molecules (soluble proteins found in the plasma), which specifically bind to the IL-1RA reduce the efficacy of the IL-1RA. The present invention provides means and methods for discarding a part of the plasma containing IL-1RI—which may potentially bind and inhibit IL-1RA, the remaining IL-1RA preparation is of greater potency.

It is herein acknowledged that the present invention provides means and methods for not only producing high concentrations and amounts of IL-1RA., but the IL-1RA so produced is of high efficacy.

This is a soluble protein found in the plasma and we believe that if we reduce its concentration by discarding part of the plasma, the IL-1RA will be more potent than in the whole blood.

In another embodiment of the invention a portion of IL-1RA substantially free of IL-1RI produced by a method of preparing autologous IL-1RA cytokine in a closed system, wherein the method comprises steps of obtaining a system selected from the group consisting of: a vessel system, a syringe system, or any combination thereof; further wherein a higher potency of the IL-1RA is obtained when the plasma containing IL-1RI molecules which may bind to IL-1RA, is discarded.

In the foregoing description, embodiments of the invention, including preferred embodiments, have been presented for the purpose of illustration and description.

They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A system for preparing autologous IL-1RA cytokine comprising:
   a. a blood collection tube;
   b. a tube cover adapted to be received over an open end of the blood collection tube for maintaining said tube closed;
   c. a portion of separation gel in the blood collection tube;
   d. an anticoagulant portion in the blood collection tube;
   e. a plasma collection syringe comprising a sharp needle configured to be inserted into the blood collection tube;
   f. a buffy coat collection syringe configured to be inserted into the blood collection tube; and
   g. an incubation tube separate from said blood collection tube with a cover, said incubation tube comprising washed and pretreated borosilicate glass beads in a size range of about 0.5-5 mm and adapted to receive contents of the buffy coat collection syringe removed from the blood collection tube;
   wherein said blood collection tube is a vacuum tube; said separation gel and said anticoagulant are in said vacuum tube; said separation gel is adapted as a barrier and as a separating element between separation tractions;
   further wherein said blood collection tube is adapted such that, when containing whole blood, after centrifugation yields separation fractions comprising, a first fraction of red blood cells sediment, a second fraction of said separation gel, a third fraction comprising white blood cells and platelets, and a fourth fraction of plasma solution.

2. The system according to claim 1, wherein said incubation tube is adapted for incubation for a sufficient time and at a temperature to yield autologous IL-1RA cytokine; said incubation tube being selected from the group consisting of: a plastic tube and a glass tube and a combination thereof.

3. The system according to claim 1, wherein said system further comprises:
   a. a filter unit connected to the plasma collection syringe having pore size of about 0.2-50 µm.

4. The system according to claim 1, further comprising a centrifuge adapted to receive said blood collection tube and perform centrifugation at 300 g to 1500 g for about 10 to about 30 minutes.

5. The system according to claim 4, wherein
   a. up to 80% of said plasma is discarded from said blood collection tube so that
   a higher potency of said IL-1RA is obtained when plasma portion containing IL-1RI molecules which bind and inhibit IL-1RA, is discarded.

6. The system according to claim 1, further comprising a stopcock adapted as a turning plug to control the flow of fluid from said plasma collection syringe to said blood collection tube.

7. The system according to claim 1, further comprising a stopcock adapted as a turning plug to control the flow of fluid from said huffy coat collection syringe to said blood collection tube.

8. The system according to claim 1, wherein said anticoagulant is a citrate-based anticoagulant, and wherein said separation gel has a density of about 1.06-1.09 g/cm$^3$.

* * * * *